US012765815B2

United States Patent

(12) United States Patent
Chase

(10) Patent No.: US 12,765,815 B2
(45) Date of Patent: Oct. 20, 2026

(54) CANNULA SENSING SYSTEM

(71) Applicant: Arnold Chase, West Hartford, CT (US)

(72) Inventor: Arnold Chase, West Hartford, CT (US)

( * ) Notice: Subject to any disclaimer, the term of this patent is extended or adjusted under 35 U.S.C. 154(b) by 0 days.

(21) Appl. No.: 17/578,674

(22) Filed: Jan. 19, 2022

(65) Prior Publication Data

US 2023/0225645 A1 Jul. 20, 2023

(51) Int. Cl.

| | |
|---|---|
| ***A61B 5/1473*** | (2006.01) |
| ***A61B 5/00*** | (2006.01) |
| ***A61B 5/145*** | (2006.01) |
| ***A61B 5/1459*** | (2006.01) |
| ***A61B 5/1486*** | (2006.01) |
| *A61B 5/1495* | (2006.01) |

(52) U.S. Cl.

CPC ...... *A61B 5/14735* (2013.01); *A61B 5/14532* (2013.01); *A61B 5/14546* (2013.01); *A61B 2562/06* (2013.01); *A61B 2562/227* (2013.01)

(58) Field of Classification Search

CPC ............ A61B 5/14735; A61B 5/14532; A61B 5/14546; A61B 2562/06; A61B 2562/227; A61B 5/14503; A61B 5/14539; A61B 5/1459; A61B 5/1473; A61B 5/14865; A61B 5/1495; A61B 5/4839; A61B 5/6848; A61B 5/6849

See application file for complete search history.

(56) References Cited

U.S. PATENT DOCUMENTS

| | | | | | |
|---|---|---|---|---|---|
| 5,720,293 | A * | 2/1998 | Quinn | A61B 5/028 | 600/549 |
| 2004/0243145 | A1* | 12/2004 | Bobo, Sr. | A61B 17/1695 | 606/129 |
| 2016/0000363 | A1* | 1/2016 | Jones | A61B 5/155 | 600/577 |
| 2018/0103882 | A1* | 4/2018 | Biederman | C12Q 1/006 | |
| 2020/0214625 | A1* | 7/2020 | Hooven | A61M 5/31 | |
| 2020/0297997 | A1* | 9/2020 | Windmiller | A61M 5/1723 | |
| 2021/0052218 | A1* | 2/2021 | Quinn | G06N 3/0445 | |

FOREIGN PATENT DOCUMENTS

| | | | | |
|---|---|---|---|---|
| AU | 2008230832 | A1 * | 10/2009 | A61B 5/14532 |
| CA | 2768106 | A1 * | 1/2011 | A61B 5/14532 |
| CN | 101227859 | A * | 7/2008 | A61B 5/00 |
| KR | 20190059135 | A * | 5/2019 | |
| WO | 2016049243 | A1 | 3/2016 | |

OTHER PUBLICATIONS

KR20190059135A—Google Patents machine translation (Year: 2019).*
Updated Google Patents translation of KR 20190059135 A (Year: 2019).*
International Search Report of corresponding PCT Application No. PCT/US2023/060604 dated Feb. 23, 2023.

* cited by examiner

*Primary Examiner* — Justin Xu
(74) *Attorney, Agent, or Firm* — McCormick, Paulding & Huber PLLC

(57) ABSTRACT

A cannula sensing system and method include a cannula having at least one biosensor configured to detect a level of one or more biomarkers in blood within a blood vessel of a patient. The biosensors are arranged at or near a distal end of a cannula inserted within the blood vessel. The biosensor may be connected to a wire arranged on and/or within a wall of the cannula.

27 Claims, 3 Drawing Sheets

CANNULA SENSING SYSTEM

TECHNICAL FIELD

The present disclosure relates to intravenous cannulas with one or more biosensors with the ability to monitor levels of one or more substances in the bloodstream of a patient.

BACKGROUND

In emergency healthcare, it is often said that "time is of the essence." When emergency medical technicians (EMTs) first interface with a patient, an initial medical assessment needs to be made. This can be especially challenging in cases where the patient is unresponsive and unable to assist the medical personnel in establishing a diagnosis. In situations such as this, prehospital intravenous (IV) access is an essential part of the EMT practice so that the EMT is in a position to stabilize the patient while in transport to a medical facility where further testing may be administered to determine an appropriate treatment protocol.

Often in such situations an intravenous infusion line is inserted in a blood vessel in order to allow fluids and/or an infused medicine to be "pushed" to the patient while they are still in transport, or in some cases a blood sample may be withdrawn for use in a present or subsequent test to be administered in a hospital setting.

Inherently, a blood sample cannot be withdrawn from a cannula concurrent with fluids being pushed to a patient, so if a parallel operation is desired then multiple cannulas must be inserted sequentially at different body site locations. Not only is this extra effort unwieldy, but it also hinders the speed at which diagnostic testing and/or drug delivery may be accomplished. Further complicating the matter, each additional IV placement increases the chance for infection or other complications.

SUMMARY

The present disclosure provides a Cannula Sensing System (CSS), which allows a single intravenous cannula insertion to provide not only traditional cannula functionality, as well as advantageously also including a simultaneous capability to test one or more blood biomarkers (e.g. a molecule, compound, electrolyte, chemical, protein, etc.). The CSS may also allow for an intravenous (IV) cannula set(s) to additionally provide for real-time readings of one or more biomarkers to medical personnel within the same venipuncture session. This ability to immediately provide venous blood testing improves upon conventional cannula systems in that empirical data may now be obtained in place of educated treatment speculation, which allows for more intelligent medical management in many emergency medical situations. In the hypothetical unresponsive patient situation mentioned above, there may be a multitude of quite varied causes for the unresponsive condition including, for example, hypoglycemia, a dangerously low blood electrolyte level, a heart attack, a drug induced coma, etc.

In each of the aforementioned emergency medical situations, there exists laboratory blood biosensors that are capable of being diagnostically instructive to medical personnel. Heretofore, while it was possible to draw blood samples and then conduct laboratory tests upon this sample, as discussed above, not only is this sampling process mutually exclusive in a traditional cannula undergoing an ongoing medical infusion, but it is also merely a "snapshot" reading in nature which is not especially helpful in monitoring a rapid progression of a critical medical situation.

As an example, currently the protocol in many medical situations calls for the immediate start of an intravenous (IV) fluid line. In a number of cases, fluids such as a saline solution or glucose are chosen and used as an initial default course of treatment.

Each year thousands of unexpected high or low blood glucose "adverse event" fatalities occur during scheduled hospital procedures due to the inability to contemporaneously monitor said patient's blood glucose readings. While systems have been developed to utilize venipunctured intravenous cannulas to get an initial snapshot blood sample glucose reading, it only provides for a one-time testing ability before the cannula is then exclusively used for its originally intended infusion purpose.

Traditionally, intravenous (IV) cannulas have been used on a stand-alone basis by healthcare professionals to infuse drugs or fluids such as saline into blood vessels. While separate biomedical sensors have been used concurrently with a limited number of patients, these additional devices require further venipunctures and/or insertions in order to work.

Each of the aforementioned insertion procedures require a high degree of skill to successfully accomplish, and require multiple venous or other device insertions that increases the amount of time required to accomplish the insertions, as well as increasing the pain and physical and emotional trauma that such multiple successive insertions cause, as well as adding additional labor costs and time required for each additional procedure as well. Insertion of a venous cannula is a painful procedure that can also lead to anxiety and stress.

A venous cannula is inserted into a vein primarily for the administration of medicines, intravenous fluids, or for initially obtaining blood samples. An arterial cannula is inserted into an artery, commonly the radial artery, and is used during major operations and in critical care areas to measure beat-to-beat blood pressure and to draw repeated blood samples. If a cannula is being used for the injection of anything, it is not available for any blood draws and external sampling that would need to be done.

A Cannula Sensing System (CSS) according to the present disclosure provides the ability to advantageously add additional functionality from within a single IV cannula insertion location. This is made possible by utilizing extremely thin wires that are molded directly into the outer walls of an infusion set tubing body. These wires extend from an electrical connector in an area proximate to a Luer lock, or other tubing connector, to a sensing location proximate the cannula delivery end. At the sensing location, the wires may connect directly to sensing probes, or they may operatively connect to electrochemical sensors.

This unique embodiment allows for an instant testing ability for several parameters as soon as the cannula is placed, without the need to physically draw blood from a vein and subsequently run the blood sample to a lab for analysis. Utilizing this system eliminates the need for disposables (needles, vials, etc.) as well as eliminating the requirement for medical personnel to have to devote time and resources on having to separately draw blood to obtain critical data which frees them up for higher priority matters.

DETAILED DESCRIPTION

Figure 1A:
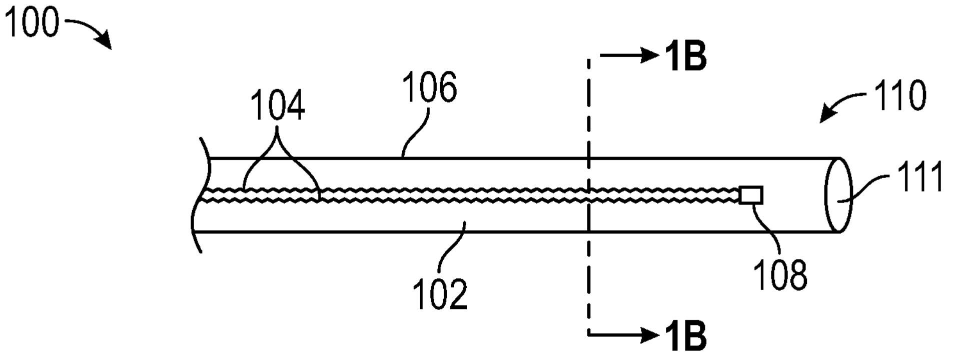
FIG. 1A shows a cannula tubing distal end of an exemplary CSS in accordance with the present disclosure.

Before the various exemplary embodiments are described in further detail, it is to be understood that the present invention is not limited to the particular embodiments described. It is also to be understood that the terminology used herein is for the purpose of describing particular embodiments only, and it not intended to limit the scope of the claims of the present application.

In the drawings, like reference numerals refer to like features of the systems and methods of the present disclosure. Accordingly, although certain descriptions may refer only to certain figures and reference numerals, it should be understood that such descriptions might be equally applicable to like reference numerals in other figures.

Figure 1B:
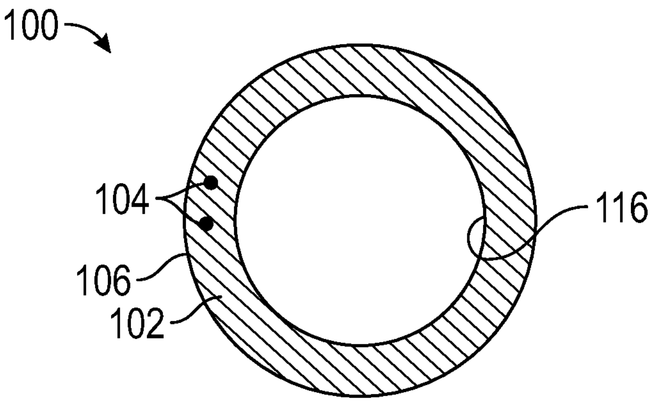
FIG. 1B shows a cross-section view of the cannula tubing of the CSS of FIG. 1A in accordance with the present disclosure.
Figure 1C:
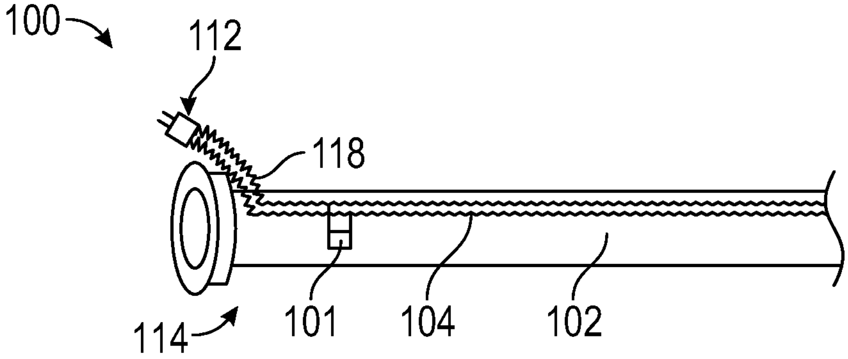
FIG. 1C shows a cannula tubing proximal end of the CSS of FIG. 1A in accordance with the present disclosure.

Referring to FIGS. 1A-1C, an exemplary embodiment of a CSS 100 is shown in accordance with the present disclosure. The CSS 100 includes a flexible (or "soft") intravenous (IV) cannula tubing 102 that may be made of any materials conventionally used for cannula tubings. Cannula tubing 102 has a first end 110 having an opening 111 for delivering any kind of intravenous medication/materials (e.g. saline water, glucose, etc.). The CSS 100 includes one or more active biosensing elements (or biosensors) 108 that may be molded on and/or within the wall 106 of the cannula tubing 102 proximate the first end 110. The CSS 100 further includes wires 104 (e.g. miniature wires) that may be molded on and/or within the wall 106 of the cannula tubing 102 to provide an operative connection to the one or more biosensing elements 108. An electrical connector 112 that is operatively connected to the wires 104 and/or active sensing element(s) 108 is arranged at a second end 114 of the tubing 102 opposite the first end 110. The active biosensing element may be, for example, a biochemical reactive device such as an area of glucose oxidase which reacts with blood to produce an electric current.

In some embodiments, by arranging and/or molding in place wires 104 at a point that is equidistant between the inner surface of the tubing 116 and the outer wall (surface) 106 of the tubing 102, the wires 104 have no negative effect whatsoever on the fluid flowing through or around the tubing, and does not change the inner or outer dimensions of the tubing. While the wires 104 are generally shown as extending in the direction of the tubing 116, in some embodiments the wire(s) 104 extend in a spiral shape such that the wire(s) 104 wrap around the periphery of the inner flow path. The wire(s) 104 can be in any other shape or arrangement along the general extension direction of the tubing 116, for example, in a zig-zag shape, sinusoidal shape, etc.

Given the low current needed to be used for biosensor 108 operation (only a few milliamperes at most in some embodiments), the wire gauge may be incredibly small (~33 gauge) while adequately handling the tasks needed. Because the wire(s) 104 may be inherently encapsulated in certain embodiments, no insulation, in either wrapped or enamel form, is necessary, thereby further decreasing the overall diameter size of each conductor. Due to the inherent physical protection afforded by the tubing 102 that surrounds the wire 104, the physical fragility of such small wires is not a factor.

Preferably, the wires 104 are configured to exit the tubing 102 outer wall 106 through a molded-in wire strain relief 118 that may also provide a physical protection in a spliced transition to a heavier gauge wire, which would ultimately terminate into the electrical connector 112 receptacle. This overall design fundamentally allows for more than a single pair of wires 104 to follow the same methodology. Commensurate with an increase in wires (or conductors) 104 is an increase in the number of biosensing elements 108 that may be accommodated.

Figure 2A:
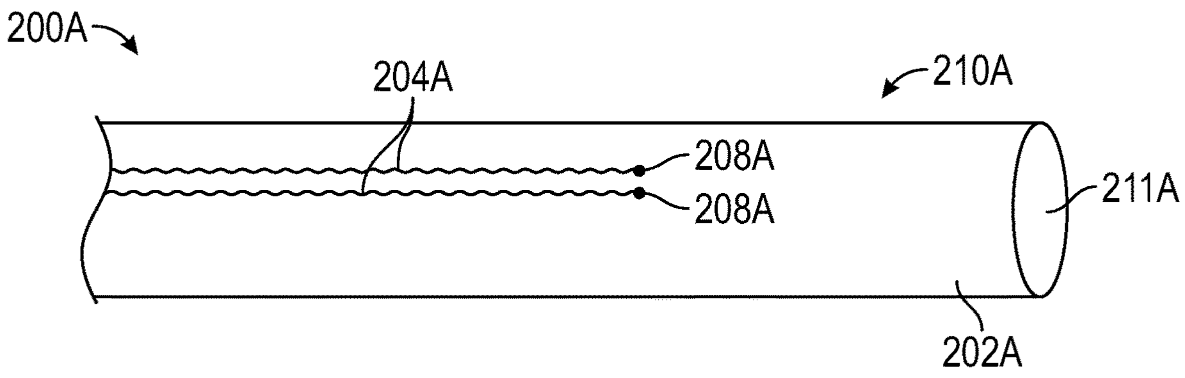
FIG. 2A shows a cannula tubing distal end of another exemplary CSS in accordance with the present disclosure.

Referring to FIG. 2A, a distal end 210A of a cannula tubing 202A of another exemplary CSS 200A is shown in accordance with embodiments of the present disclosure. The CSS 200A includes a pair of passive biosensing elements 208A that form contact points configured to directly interface with the blood in a blood vessel of a patient when the end 210A is inserted within the blood vessel. Each passive biosensing element 208A may be associated with its own wire 204A. As such, the pair of passive biosensing elements 208A in conjunction with wires 204A may form a single circuit for sensing information about the blood in the blood vessel. The passive biosensing elements 208A may be, for example, conductive elements that are designed to make a direct blood conductivity measurement (analogous to an ohmmeter for blood). The more electrolytes in the blood at any given time, the greater the blood conductivity. The blood conductivity, thus, becomes a proxy for the electrolyte level. A blood conductivity over a predetermined threshold may be recognized as an indication of extreme dehydration by a user of the CSS 200A or a controller of the CSS 200A.

Figure 2B:
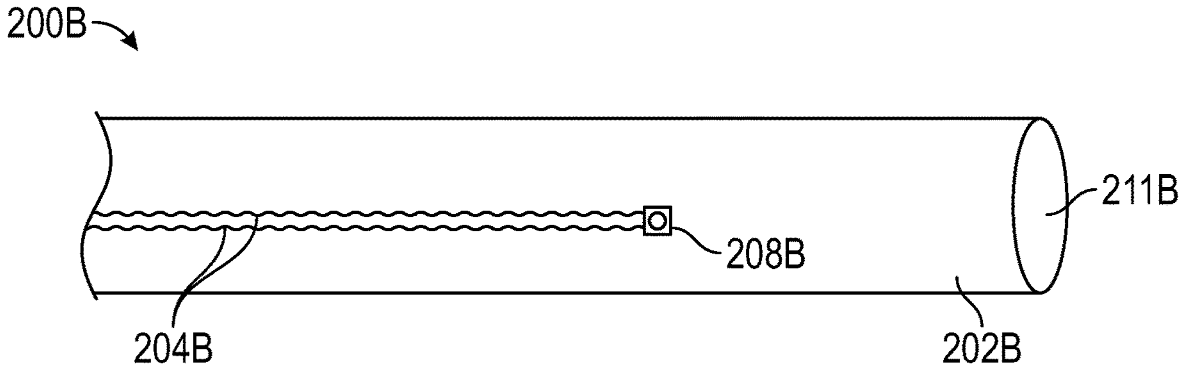
FIG. 2B shows a cannula tubing distal end of another exemplary CSS in accordance with the present disclosure.

Referring to FIG. 2B, a distal end 210B of a cannula tubing 202B of another exemplary CSS 200B is shown in accordance with embodiments of the present disclosure. In this embodiment, biosensor 208B is coupled between wires 204B thereby completing the electrical circuit.

Figure 2C:
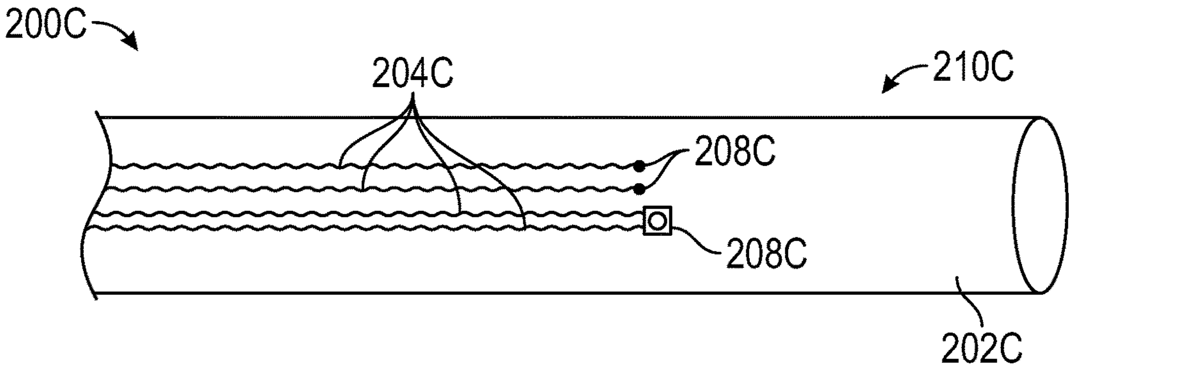
FIG. 2C shows a cannula tubing distal end of another exemplary CSS in accordance with the present disclosure.

Referring to FIG. 2C, a distal end 210C of a cannula tubing 202C of another exemplary CSS 200C is shown that is a combination of the embodiments shown in FIGS. 2A and 2B in accordance with embodiments of the present disclosure. In other words, this embodiment includes a pair of passive direct sensing contacts 208C each connected to a wire 204C and an active biosensor 208C with two wires 204C connected thereto.

Figure 2D:
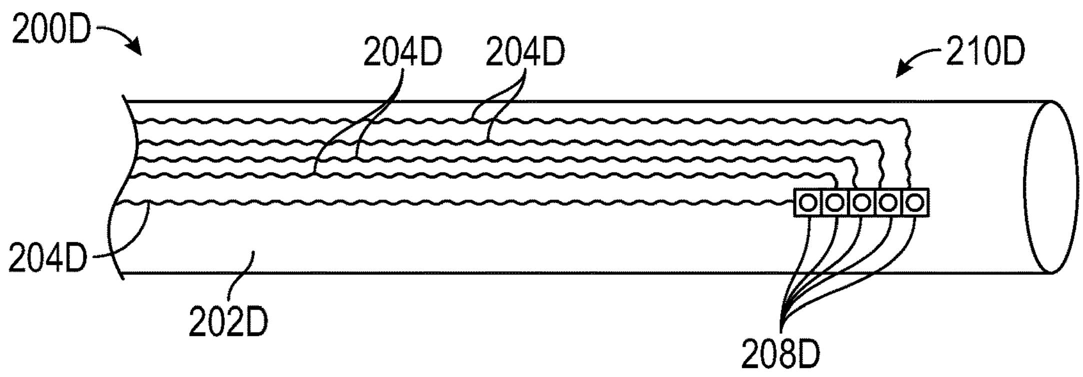
FIG. 2D shows a cannula tubing distal end of another exemplary CSS in accordance with the present disclosure.

Referring to FIG. 2D, a distal end 210D of a cannula tubing 202D of another exemplary CSS 200D is shown in accordance with embodiments of the present disclosure. Multiple biosensors 208D in this embodiment are arranged proximate the distal end of the cannula tubing 202D. As shown in FIG. 2D, the biosensors 208D may be oriented in a linear fashion along the tubing 202D in a longitudinal direction of the tubing 202D. Other arrangements of the biosensors 208D are possible, including for example, circumferentially spacing biosensors 208D around the distal end of the tubing 202D. A pair of wires 204D are operatively connected to each respective biosensor 208D (although, for simplicity, each pair of wires 204D is shown as only one line in FIG. 2D). In some embodiments, two or more biosensors 208D may each share a single wire thus allowing for a common return lead wire 204D allowing for a reduced number of needed wires 204D and/or allowing an increased number of biosensors 208D.

Figure 2E:
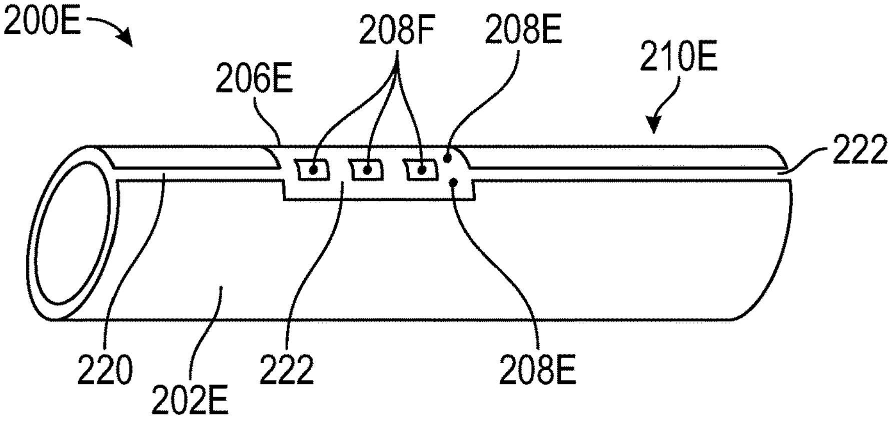
FIG. 2E shows a cannula tubing distal end of another exemplary CSS in accordance with the present disclosure.

Referring to FIG. 2E, a distal end 210E of a cannula tubing 202E of another exemplary CSS 200E is shown in accordance with embodiments of the present disclosure. In this embodiment, the CSS 200E comprises one or more slight concave linear first groove(s) 220 proximate to the contacts 208E and bio-sensors 208F to help direct and assist a fresh flow of blood to flow by the biocontacts 208E and biosensors 208F. Biosensors 208F may be located flush to the outer wall 206E in one or more second groove(s) 222 (the second groove(s) 222 optionally being larger than the first groove(s) 220). Advantageously, this continuing blood flow allows the sensors 208F to continuously receive updated readings which not only are beneficial in an empirical sense, but also allow for trending information to be established. More than one first groove 220 and/or more than one second groove 222 may be arranged around the circumference of the cannula tubing 202E. The groove(s) 220, 222 may be configured in some embodiments to be concave or slightly concave. The groove(s) 220, 222 are configured to help direct and assist a fresh flow of blood across the biosensor(s) which may be located within a larger "carved out" area (i.e. an area of the groove having a larger width and/or size than areas of the groove outside the carved out area, e.g. in an intermediate portion) that is flush with the outer wall of the cannula tubing. Thus, the bottom of the groove(s) 220, 222 be depressed from the outer most portion of the outer wall in a radial direction of the cannula tubing 202.

Figure 3:
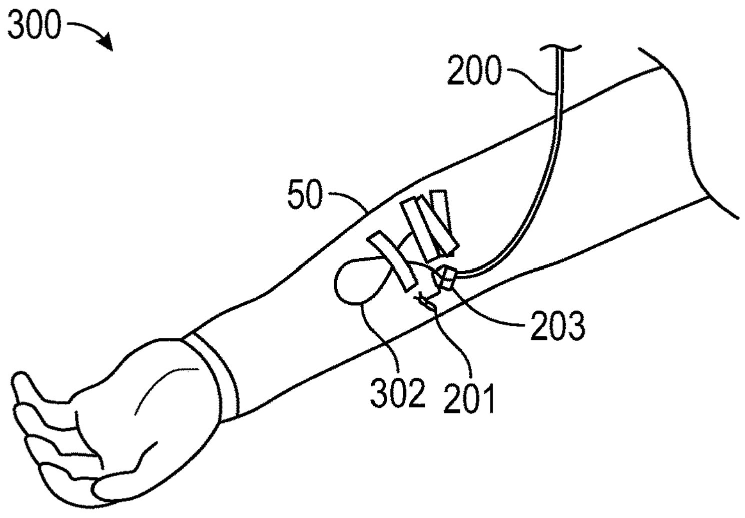
FIG. 3 shows an exemplary CSS inserted into a blood vessel of an arm of a patient in accordance with the present disclosure.

Referring to FIG. 3, an exemplary CSS 300 is shown inserted into a blood vessel of an arm 50 of a patient in accordance with the present disclosure.

The biosensing elements 208 may be configured as metallic contact points 208A configured to provide true in situ testing. The metallic contact points of the biosensing elements 208A may be made of any metal capable of providing sensing function such as, for example and without limitation, stainless steel, copper, yellow gold, platinum, sterling silver, gold plated contact points, or other metals that are less likely to cause bodily irritation when they are located in the bloodstream of a patient in order to directly measure blood characteristics such as electrolytes (e.g. sodium, etc.), pH, etc., or the biosensors 208B may comprise reagents in various physical forms that react to specific biomarkers to generate a small electric current or data. Regardless of actual sensor embodiment, an advantage of a CSS according to the present disclosure is that the sensing points and/or sensors in the cannula reside in a vein that has a continuing flow of blood, and as such are continuously exposed to a fresh representation of updated blood characteristics.

In some embodiments, a CSS 100, 200, 300 may be configured to monitor a single parameter such as blood glucose levels, the system 100, 200, 300 can accommodate a greatly increased number of other simultaneously sensed parameters such as pH levels, electrolyte levels, cardiac troponin level sensing, ketone level sensing, opiate sensing, or other electrochemical sensed biomarkers. As new blood sensor technology evolves, there may be other types of sensors that may be readily incorporated into the tubing of the CSS as disclosed herein.

According to certain embodiments, the biosensor data may be collected and/or displayed on a continuous (or semi-continuous) basis, and a data reading device which may be plugged into, and/or operatively connected to, the CSS electrical connector 112 (FIG. 1C) may allow EMT personnel to also avail themselves of either instant empirical data, and/or provide a rate of change/direction of change indication of the one or more monitored parameters as well.

Since in many cases the trending information can be of significant diagnostic value, one preferred embodiment of a CSS would include a small non-volatile memory chip 101 (FIG. 1C) inside the tubing 102, 202 or strain relief 118 which would store the recent data for each sensor channel. Since the connector 112 and memory chip 101 would travel with the patient to a hospital environment, upon arrival at a hospital, a download device at a hospital would be able to be plugged into the electrical connector 112 of tubing 102, 202, 302 (or otherwise communicate, e.g. wireless means) and provide the emergency hospital personnel with an instant initial situation awareness of the patient's biomarkers history prior to arrival, simultaneously with continued "real-time" data. This would also allow emergency transportation personnel to concentrate on relaying other possibly relevant patient or ambient condition information to the hospital staff. The data reader in ambulances and hospitals would be equipped with a real time clock (RTC) that would allow the sensor data readings to be time-stamped (in any type of time-stamped configuration), stored, (and subsequently read) for precise trend analyses by later medical personnel, and/or the data readings can be time-stamped (in any type of time-stamped configuration), stored (and subsequently read) from the memory chip 101 and/or controller of the CSS.

The CSS biosensor data may also function to allow for an intelligent closed loop hydration/electrolyte/drug delivery modulation to match an infusion delivery rate of therapy agents corresponding to real-time data readings rather than utilizing a less than ideal traditional/fixed open-loop therapy agent delivery rate. Since the biosensors 108, 208 are purposefully located "upstream" of the (distal) delivery opening by inserting the CSS tubing 102, 202, 302 into a blood vessel, there would be no cross-contamination effect by the therapy agent delivery upon the levels monitored by the biosensor(s) 108, 208.

Even though some hospitals may be equipped with "fingerstick" blood glucose meters, these devices merely provide snapshots of instant blood glucose levels. If insulin is infused into a patient during a procedure, then there is a high likelihood of ongoing insulin level mismatch between a body's insulin need and the supplied insulin rate. Also, anesthesia and other procedural stresses can affect blood glucose levels in diabetic patients in unexpected ways. While there have been some attempts at using hospital versions of consumer "continuous" blood glucose monitors, the extended "warm up" times and the fact that they are actually measuring interstitial fluid as a proxy for true blood glucose monitoring makes then far inferior to the use of CSS for in-procedure glucose monitoring.

While the aforementioned discussion centered on the use of the CSS for field to hospital transportation benefit, nothing limits its use to pre-hospital use. A CSS may be equally beneficial during routine hospital procedures in eliminating the need for frequent blood draws to assess a patient's continuing condition.

Although CSS adds additional functionality capability, nothing prevents a CSS cannula set from being used in a conventional (non-sensing) manner as well. CSS cannula sets may be produced with numerous variations, specifically, with either a single biomarker test capability or the capability to monitor a plurality of biomarker parameters (e.g. the ability up to six or more test capability). Just as multiple parameter (ten or more testing parameters) urine test strips may be primarily used to test for just a single biomarker of interest, having the other parameters present at times may prove highly beneficial in a clinical setting. As such, utilizing a CSS set with multiple biomarker parameters may prove to be of unexpected value. Unlike individually ordered traditionally drawn tests, with a CSS no additional effort is needed to accomplish additional parameter testing. Additionally, a CSS may be used to monitor nutrients and infuse nutrients such as glucose in order to intelligently optimize an nutrient infusion rate.

The foregoing description of embodiments of the present disclosure has been presented for the purpose of illustration and description. It is not intended to be exhaustive or to limit the invention to the form disclosed. While the exemplary application has focused on particular embodiments, obvious modifications and variations are possible in light of the above disclosure and should be considered within the scope and spirit of the present disclosure. The embodiments described were chosen to best illustrate the principles of the invention and practical applications thereof to enable one of ordinary skill in the art to utilize the invention in various embodiments and with various modifications as suited to the particular use contemplated.

What is claimed is:

1. A cannula sensing system comprising:

a cannula having a distal end defining an opening;

one or more biosensors arranged on and/or within an outer wall of the cannula; and a memory storage device embedded in the cannula;

wherein the one or more biosensors are configured to generate biosensor data based on a detected level of one or more biomarkers in blood;

wherein the cannula is configured to deliver intravenous medication and/or fluid materials into a blood vessel simultaneously while the one or more biosensors are detecting the detected level of the one or more biomarkers in blood;

wherein the biosensor data is configured to be stored in the memory storage device of the cannula;

wherein the outer wall of the cannula defines a groove extending in a longitudinal direction of the cannula, and the one or more biosensors are arranged within the groove which allows for free blood flow past each biosensor;

wherein one or more parts of the groove comprises an intermediate portion having a larger width and/or depth than areas of the groove outside of the intermediate portion, and the one or more biosensors are arranged in the intermediate portion; and wherein the intermediate portion and the areas of the groove outside of the intermediate portion each have a longitudinal extension extending in the longitudinal direction.

2. The cannula sensing system according to claim 1, wherein the cannula is flexible.

3. The cannula sensing system according to claim 1, wherein the one or more biomarkers comprises glucose.

4. The cannula sensing system according to claim 1, wherein the one or more biomarkers comprises an electrolyte.

5. The cannula sensing system according to claim 1, further comprising a wire arranged on and/or within the outer wall of the cannula, wherein the wire is connected to the one or more biosensors.

6. The cannula sensing system according to claim 5, wherein the one or more biosensors are configured to send the biosensor data through the wire.

7. The cannula sensing system according to claim 5, wherein the one or more biosensors are arranged at or near the distal end of the cannula.

8. The cannula sensing system according to claim 5, wherein the wire extends to a proximal end of the cannula.

9. The cannula sensing system according to claim 5, wherein the wire is configured to be connected to a connector arranged at a proximal end of the cannula.

10. The cannula sensing system according to claim 5, wherein the wire is embedded within the cannula.

11. The cannula sensing system according to claim 5, further including a wire strain relief configured to transition the initial size wire to a heavier gauge wire.

12. The cannula sensing system according to claim 5, wherein a first and a second wire are arranged on and/or within the outer wall of the cannula, and the first and the second wires are connected to one of the one or more biosensors to form a closed circuit.

13. The cannula sensing system according to claim 1, wherein the one or more biosensors comprise a metallic direct blood contact sensing point.

14. The cannula sensing system according to claim 1, further comprising an additional biosensor arranged on and/or within the outer wall of the cannula, wherein the additional biosensor is configured to generate additional biosensor data based on a detected level of one or more additional biomarkers.

15. The cannula sensing system according to claim 14, wherein the one or more additional biomarkers are different than the one or more biomarkers.

16. The cannula sensing system according to claim 1, wherein the one or more biosensors utilize an electrochemical sensed biomarker reagent sensing detector to detect the level of the one or more biomarkers.

17. The cannula sensing system according to claim 1, wherein the one or more biosensors are configured for real-time, continuous, wireless communication with an external database.

18. The cannula sensing system according to claim 1, wherein the one or more biosensors include a plurality of biosensors arranged longitudinally at a distal end of the cannula.

19. The cannula sensing system according to claim 1, further comprising a data reader configured for receiving data from the one or more biosensors.

20. The cannula sensing system according to claim 19, wherein the data reader is further configured to associate the data received from the one or more biosensors with time stamp data.

21. The cannula sensing system according to claim 1, wherein the memory storage device is configured to store the biosensor data in a time-stamped configuration.

22. The cannula sensing system according to claim 1, wherein the one or more biosensors are configured to generate the biosensor data based on the detected level of the one or more biomarkers in blood that comes into contact with an exterior surface of the outer wall of the cannula.

23. A set of cannula sensing systems comprising:

a plurality of cannulas, each cannula of the plurality of cannulas including a biosensor arranged on and/or within an outer wall of the respective cannula and a memory storage device embedded in the cannula, and each cannula having a distal end defining an opening;

wherein each biosensor of each cannula of the plurality of cannulas is configured to generate biosensor data based on a detected level of one or more biomarkers in blood;

wherein the one or more biomarkers is different for each cannula of the plurality of cannulas;

wherein each cannula is configured to deliver intravenous medication and/or fluid materials into a blood vessel simultaneously while the one or more biosensors for the respective cannula are detecting the detected level of the one or more biomarkers in blood;

wherein the outer wall of each cannula defines a groove extending in a longitudinal direction of the respective cannula, and the one or more biosensors of each cannula are arranged within the respective groove which allows for free blood flow past each biosensor;

wherein one or more parts of each groove comprises an intermediate portion having a larger width and/or depth than areas of the respective groove outside of the intermediate portion, and the one or more biosensors of each cannula are arranged in the respective intermediate portion; and wherein the intermediate portion of each cannula and the areas of the groove outside of the intermediate portion of each cannula each have a longitudinal extension extending in the longitudinal direction of the respective cannula.

24. The set according to claim 23, wherein the biosensor of one cannula of the plurality of cannulas is configured to detect a level of glucose.

25. The set according to claim 23, wherein the biosensor of one cannula of the plurality of cannulas is configured to detect a level of electrolyte.

26. A method of using a cannula sensing system comprising:

inserting a distal end of a cannula into a blood vessel of a patient, the cannula including a biosensor arranged on and/or within an outer wall of the cannula configured to detect a biomarker in blood;

delivering intravenous medication and/or fluid materials into the blood vessel through the cannula;

detecting, with a biosensor, a biomarker in blood within the blood vessel; and storing biosensor data in a memory storage device embedded in the cannula;

wherein the delivering and the detecting occur simultaneously;

wherein the outer wall of the cannula defines a groove having a longitudinal extension extending in a longitudinal direction of the cannula, and the biosensor is arranged within the groove which allows for free blood flow past the biosensor;

wherein one or more parts of the groove comprises an intermediate portion having a larger width and/or depth than areas of the groove outside of the intermediate portion, and the biosensor is arranged in the intermediate portion; and wherein the intermediate portion and the areas of the groove outside of the intermediate portion each have a longitudinal extension extending in the longitudinal direction.

27. The method according to claim 26, wherein the biosensor is arranged at or near the distal end of the cannula.

* * * * *